United States Patent
Yanof et al.

(10) Patent No.: US 11,317,823 B2
(45) Date of Patent: May 3, 2022

(54) DETECTION OF ELECTROMAGNETIC FIELD INTERFERENCE

(71) Applicant: THE CLEVELAND CLINIC FOUNDATION, Cleveland, OH (US)

(72) Inventors: Jeffrey H. Yanof, Solon, OH (US); Karl West, Geneva, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 334 days.

(21) Appl. No.: 16/461,407

(22) PCT Filed: Nov. 16, 2017

(86) PCT No.: PCT/US2017/062064
§ 371 (c)(1),
(2) Date: May 16, 2019

(87) PCT Pub. No.: WO2018/094080
PCT Pub. Date: May 24, 2018

(65) Prior Publication Data
US 2019/0343421 A1    Nov. 14, 2019

Related U.S. Application Data

(60) Provisional application No. 62/422,654, filed on Nov. 16, 2016.

(51) Int. Cl.
*A61B 5/06* (2006.01)
*A61B 5/00* (2006.01)

(52) U.S. Cl.
CPC .............. *A61B 5/062* (2013.01); *A61B 5/742* (2013.01); *A61B 5/7405* (2013.01); *A61B 5/746* (2013.01); *A61B 5/7455* (2013.01)

(58) Field of Classification Search
CPC ........ A61B 5/062; A61B 5/7405; A61B 5/742; A61B 5/7455; A61B 5/746; A61B 2034/2051; A61B 2560/0238
See application file for complete search history.

(56) References Cited

U.S. PATENT DOCUMENTS 6,129,668 A * 10/2000 Haynor .................... A61B 5/06
                                                              128/899
8,478,382 B2 * 7/2013 Burnside ................. A61B 5/06
                                                              600/424

(Continued)

OTHER PUBLICATIONS

PCT International Search Report and Written Opinion for corresponding Application Serial No. PCT/US2017/062064, dated Feb. 8, 2018, pp. 1-12.

*Primary Examiner* — Sanjay Cattungal
(74) *Attorney, Agent, or Firm* — Tarolli, Sundheim, Covell & Tummino LLP (57) ABSTRACT

An example system includes a distortion reference sensor (DRS) device attachable to a surface adjacent a region of interest within the patient. The DRS device includes at least two sensor coils arranged at a predetermined angle relative to each other and at a predetermined spatial position in a three-dimensional space relative to each other. The system also includes a computing device to determine a sensed angle and a sensed spatial position of the at least two sensor coils in the three-dimensional coordinate system in response to application of an electromagnetic field. Electromagnetic field distortion is indicated based on a difference between the predetermined angle and the sensed angle and/or the predetermined spatial position and the sensed spatial position exceeding an expected difference value.

26 Claims, 6 Drawing Sheets

(56) References Cited

U.S. PATENT DOCUMENTS

| | | | |
|---|---|---|---|
| 8,644,907 B2* | 2/2014 | Hartmann | A61B 17/1615 |
| | | | 600/424 |
| 8,781,555 B2* | 7/2014 | Burnside | A61B 8/0841 |
| | | | 600/424 |
| 2001/0047133 A1* | 11/2001 | Gilboa | A61B 34/20 |
| | | | 600/429 |
| 2002/0165448 A1* | 11/2002 | Ben-Haim | A61N 1/36564 |
| | | | 600/424 |
| 2006/0122497 A1 | 6/2006 | Glossop | |
| 2006/0211914 A1* | 9/2006 | Hassler | A61M 39/0208 |
| | | | 600/37 |
| 2008/0012553 A1 | 1/2008 | Shalgi et al. | |
| 2008/0079421 A1 | 4/2008 | Jensen | |
| 2014/0051983 A1* | 2/2014 | Schroeder | A61B 34/20 |
| | | | 600/424 |

\* cited by examiner

DETECTION OF ELECTROMAGNETIC FIELD INTERFERENCE

CROSS-REFERENCE TO RELATED APPLICATIONS

This application claims the benefit of U.S. Provisional Application No. 62/422,654, filed 16 Nov. 2016 and entitled, "IMPROVING THE ACCURACY OF ELECTROMAGNETIC TRACKING OF ENDOVASCULAR DEVICES". The entirety of this provisional application is hereby incorporated by reference for all purposes.

TECHNICAL FIELD

This disclosure relates generally to detecting electromagnetic field interference, which can be used for improving the accuracy of electromagnetic tracking of medical devices.

BACKGROUND

Electromagnetic tracking can be used to track the position and orientation of a medical device in a patient's body during a medical procedure. For example, an endovascular device (e.g., a wire, a catheter, or the like) can be electromagnetically tracked within a patient's vasculature during an angiography procedure. However, such electromagnetic tracking can experience electromagnetic field distortion, which can cause inaccuracies in the position data and the transformations calculated by the tracking system. For example, the electromagnetic field distortion can be due to the presence of metals within the electromagnetic field or other field generating devices. Such electromagnetic field distortion may present a large problem, such as in situations when electromagnetic tracking systems are used in connection with C-arm angiography.

SUMMARY

This disclosure relates generally to detecting electromagnetic field distortion. This disclosure describes systems, methods and devices that can be used to detect an electromagnetic field distortion and to alert a user of the electromagnetic field distortion to facilitate tracking medical devices through a patient's body with a higher accuracy. As an example, the systems, methods, and devices of this disclosure can be used in connection with tracking an endovascular device during a C-arm angiography procedure.

In an example of this disclosure, a system is described. The system includes a distortion reference sensor (DRS) device attachable to a surface of a patient adjacent a region of interest within the patient. The DRS device includes at least two sensor coils arranged at a predetermined angle and a predetermined spatial position in a three-dimensional space relative to each other. The system also includes a computing device to determine a sensed angle and a sensed spatial position of the at least two sensor coils in response to application of an electromagnetic field. Electromagnetic field distortion is indicated based on a difference between the predetermined angle and the sensed angle and/or the predetermined spatial position and the sensed spatial position exceeding an expected difference value.

In another example of this disclosure, a method is described. The method includes attaching a distortion reference sensor (DRS) device to a surface of a patient, adjacent a region of interest within the patient. The DRS device includes at least two sensor coils arranged at an angle relative to each other and at a predetermined spatial position in three-dimensional space relative to each other. The DRS device can be exposed to an electromagnetic field, and a sensed angle and sensed spatial position of the at least two sensor coils in three-dimensional space can be determined relative to each other. An electromagnetic field distortion due to the electromagnetic field can be estimated based on a difference between the predetermined angle and the sensed angle and/or the predetermined spatial position and the sensed spatial position exceeding an expected difference value.

DETAILED DESCRIPTION

This disclosure relates generally to detecting electromagnetic field distortion. As a result of detecting such field distortion, actions can be implemented to improve the accuracy of electromagnetic tracking of the position and/or orientation of a device affixed with one or more tracking sensors, such as during a medical procedure. For example, an endovascular device, such as a wire, a catheter, or the like, can be electromagnetically tracked within a patient's vasculature during an angiography procedure. Such electromagnetic tracking can experience electromagnetic field distortion (also referred to as electromagnetic interference), which can cause inaccuracies in the calculation of position and/or orientation of the device due to the presence of field generating devices (e.g., secondary field due to eddy currents induced in the C-arm components by a primary electromagnetic field generator used for tracking) or metals (e.g., surgical tools) that may be utilized during the medical procedure, such as sources and detectors used during imaging procedures.

Systems and methods disclosed herein can be used to detect electromagnetic field distortion and to alert a user of the electromagnetic field distortion to facilitate tracking a medical device through a patient's body with an improved accuracy. For example, the systems, methods, and devices can improve the tracking accuracy of an endovascular device during a C-arm angiography procedure. The systems, methods, and devices of the present disclosure can monitor the electromagnetic field distortion using a distortion reference sensor (DRS) device. The DRS device includes sensor coils that are positioned at a known orientation (predetermined angle and predetermined spatial position in a three-dimensional coordinate system) relative to each other. The DRS device can be positioned at a known orientation relative to the patient, which orients its sensor coils (also referred to as sensors) within the DRS device relative to both an electromagnetic field generator of the tracking system and a C-arm or other sources of field distortion. When exposed to a magnetic field, if there is magnetic field distortion, a sensed indication of the angle and/or the spatial position of the sensors can be different from the predetermined angle and/or the predetermined spatial position. When the difference exceeds an expected difference value (a threshold value), a warning message is provided to a user, such as a physician performing the medical procedure or another individual associated with the medical procedure.

Figure 1:
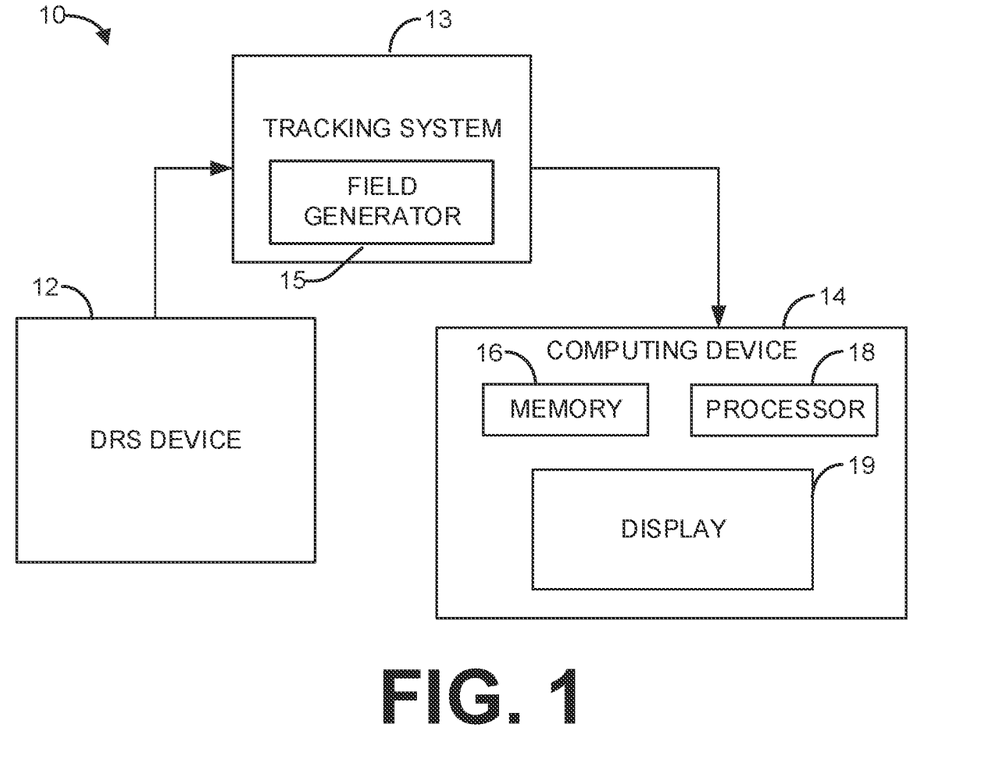
FIG. 1 depicts a block diagram of an example of a system to detect an electromagnetic field distortion and to alert a user of the electromagnetic field distortion.

FIG. 1 depicts an example of a system 10 to detect an electromagnetic field distortion and to alert a user of the electromagnetic field distortion. The electromagnetic field distortion can be caused by an instrument that includes a metal portion being within an electromagnetic field used to track a medical device through a patient's body. The electromagnetic field distortion can have negative effects on the tracking of a medical device. The system 10 includes a DRS device 12 to detect the electromagnetic field distortion, a tracking system 13 to provide the electromagnetic field (including field generator 15) and a computing device 14 to determine existence of electromagnetic field distortion and to alert the user of the electromagnetic field distortion. Although the system 10 can be utilized to detect an electromagnetic field distortion when different types of medical devices equipped with tracking sensors are tracked within a patient's body, the system 10 will be described herein in connection with the specific example of tracking an endovascular device equipped with a tracking sensor through a patient's vasculature during a C-arm angiography procedure. The DRS device 12 can be a standard device in a specific size for a certain medical procedure. However, the DRS device 12 can be made in different sizes for different patients and/or different medical procedures. The DRS device 12 can also be specifically configured to a specific patient based on a pre-operative imaging study. Additionally, although only a single DRS device 12 is described herein, it will be understood that two one or more DRS devices can be placed at different locations and/or orientations relative to a patient and/or an operating table.

The DRS device 12 is attachable to a surface aligned and oriented relative to a region of interest within a patient. An axis of the DRS device 12 can be aligned with at least one structure within the region of interest. For example, the DRS device 12 can be attachable to a skin surface of a patient. As another example, the DRS device 12 can be placed on a surface of an operating table near or adjacent to the region of interest within the patient. By aligning and orienting the DRS device 12 with respect to a patient, the DRS device 12 can be aligned and oriented with respect to a moveable portion of a device related to a medical procedure, such as a C-arm related to a C-arm angiography procedure. As an example, the DRS device 12 (or a portion of the DRS device 12) can be aligned with at least one structure of interest for the medical procedure. For example, the DRS device 12 includes two or more sensor coils having a predetermined spacing and orientation relative to each other. The DRS device 12 can be connected to provide outputs to the tracking system 13, which provides tracking data to the computing device 14 for further processing, such as disclosed herein. In either case, the DRS device can be specifically oriented to detect and mitigate the worst-case interference caused by the C-arm or other field-influencing objects.

Figure 2:
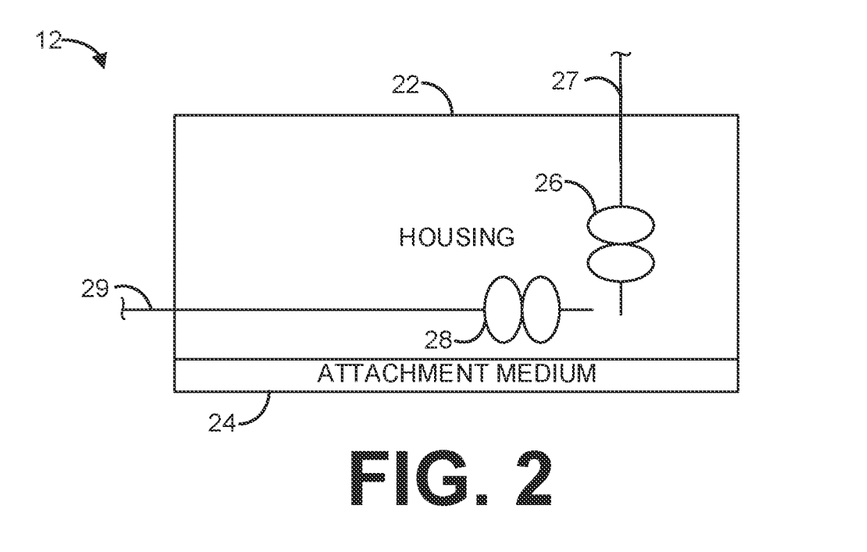
FIG. 2 depicts a block diagram of an example of a distortion reference sensor (DRS) device that can be used in the system of FIG. 1.

An example of the DRS device 12 is shown in greater detail in FIG. 2. The DRS device 12 can include a housing 22, which is illustrated as having a rectangular cross-section. However, it will be understood that the housing 22 can have any type of three-dimensional shape, including, but not limited to, a box, a prism, a sphere, a star, or the like. The housing 22 can be constructed as a solid or hollow material. In some examples, the material can be translucent. In other examples, the material can be opaque. The material can include, for example, a biocompatible polymer, a biocompatible glass, or any other type of biocompatible material that is electrically non-conductive as to not interfere with the receipt of electromagnetic field by one or more sensor coils disposed in the housing 22.

The DRS device 12 can also include an attachment medium 24 that can facilitate affixing of the DRS device 12 to a surface. The surface can be an outer surface of the patient's skin or to a surface of a table where the medical procedure is occurring. The attachment medium 24 can be any biocompatible mechanism that is electrically non-conductive and that can affix the housing 22 to the surface, including an adhesive, a clip, or the like. The attachment medium 24 can be along an entire edge of the housing 22 that contacts the patient. When used to attach the DRS device 12 to the patient's skin, the attachment medium 24 need only be of a size that is sufficient to stabilize the housing 22 in a position on the surface of the patient's skin and, in some examples, allow for removability from the skin following the procedure.

At least two sensor coils (also referred to herein as "sensors") can be arranged at a predetermined spatial distance and angle relative to each other that is fixed within the housing 22. For example, the housing 22 provides a volume of nonconductive material (e.g., a non-conductive polymer or composite material) that encapsulates sensor coils 26, 28 to maintain them at a known fixed relative position and angle. Each of the sensor coils 26, 28 can have an output that is electrically connected (e.g., via a shielded cable or other conductor 27, 29) to the tracking system 13. Two sensor coils 26, 28 are illustrated in the example of FIG. 2 for ease of illustration and explanation. However, it will be understood that the housing 22 can include three or more sensor coils in other examples.

By way of example, when used in connection with C-arm angiography, the DRS device 12 may include two or three mutually orthogonal sensor coils. In response to an electromagnetic field (e.g., generated by tracking system 13), each sensor provides a sensor signal to the tracking system that computes tracking data specifying the position and orientation of each sensor in the 3D coordinate system of the tracking system. The computing device 14 thus can process the tracking data derived from the DRS device to report an inter-sensor distance, such as based on the distance from AP (anterior-posterior) to H/F (head-foot), and from Lateral to H/F.

In other examples, the DRS device 12 may include a single sensor coil to measure distortion quantitatively. The single sensor would be arranged in a fixed, stationary position and orientation, such as when affixed to the surface of an angiography table. In this case, the distortion associated with a five DoF sensor can be independently computed, provided that position data is collected a priori with the C-arm in the "storage" position for a present table position.

Also, the stationary sensor would not be susceptible to respiratory or gross patient motion. However, a disadvantage of locating the reference sensor coil on the angiography table is that it may not be as close to the secondary electromagnetic field and therefore may not be as predictive of electromagnetic distortion at the tracking sensor. To compensate for this, the DRS device 12 could be mounted on an extension arm that is attached to the table.

An alternate example to monitor the C-arm position includes reading the C-arm position from the DICOM header of projection images generated by the Angiography system; but this would require the use of fluoroscopy or another imaging modality to determine the angulation of the C-arm and may not include the table position. The reference sensor(s) in the DRS device 12 can also be used to detect un-anticipated metal interference such as metal surgical tools being introduced into the surgical field.

By way of further example, with reference to FIGS. 1 and 2, the tracking system 13 is coupled to each of the sensor coils 26, 28 of the DRS device 12 and to one or more tracking sensors mounted to a guidewire or other endovascular device. The field generator 15 provides a primary electromagnetic field to induce current in the sensor coils, which the tracking system 13 uses to determine position and orientation of each sensor coil. The magnitude of current induced in each sensor, and thus tracking accuracy within the measurement volume, depends on its orientation relative to the field generator. Similarly, the C-arm provides a secondary field that also can induce current in each sensor, which depends on the orientation of the sensor relative to the C-arm.

In this example, one of the sensor coils 28 of the DRS device 12 is aligned to extend longitudinally along an anterior-posterior (AP) direction of the patient (which, e.g., can be most sensitive to the C-arm's secondary field induced in the C-arm's flat panel). Another of the sensor coils 26 of the DRS device 12 can be aligned to extend longitudinally along the head-foot (HF) direction of the patient (which is optimal for the primary field and can be least susceptible to the secondary field with the C-arm in the AP position). Thus, when the the C-arm is in the AP position, it is aligned to induce a higher current in the with sensor coil that is also aligned in the AP axis 28. This alignment in the AP direction results in increased sensitivity of the sensor coil 28 to eddy currents from the C-arm (also in the AP direction) that adversely affect the accuracy of the tracking data. Thus, the DRS device 12 detects distortion with maximal sensitivity (e.g., via differential effects on the two mutually perpendicular sensors with set orientation relative to the EM generator and C-arm) due to the secondary field from the C-arm, which changes the sensed distance and/or angle between the sensor coils (e.g., from its calibrated distance of zero after subtracting the 3D difference vector of the sensors' position measured with the C-arm in the storage position). The systems and methods herein thus further provide guidance to a user in response to detecting such distortion, such as to suggest that a user tilt the C-arm to a position having reduced distortion on the sensor coil. In this way, the system 10 can track, indirectly, the position of the C-arm relative the DRS device and provide guidance to rotate the C-arm (e.g., from the AP position to the Right Anterior Oblique or Left Anterior Oblique positions when targeting an artery that is approximately aligned with the AP axis), such that its secondary field induces less current in the sensor coils 26, 28, thereby increasing tracking accuracy of tracked devices in the patient's body.

Figure 3:
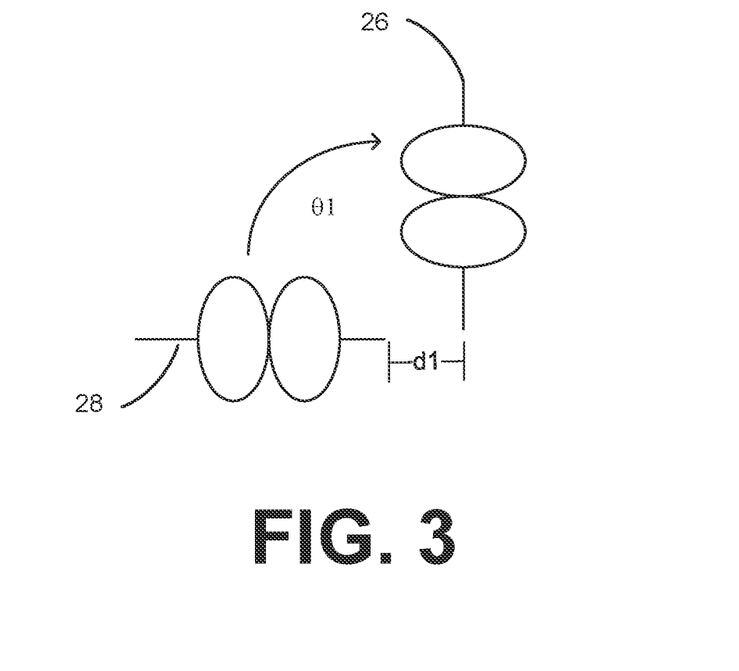
FIG. 3 depicts an example configuration of two sensors that can be located within the housing of the DRS device of FIG. 2.

As illustrated in the example of FIG. 3, the DRS device includes sensor coils 26, 28 are at a predetermined angle (θ) relative to one another and separated by a predetermined spatial position (d1). The angle and spatial position of the sensor coils 26, 28 can be relative to a Cartesian coordinate system, such as the coordinate system shown in FIG. 4. The same would be true with more sensor coils—individual sensor coils need to be at a predetermined angle relative to one another and at a predetermined spatial position relative to one another in three-dimensional space.

Figure 4:
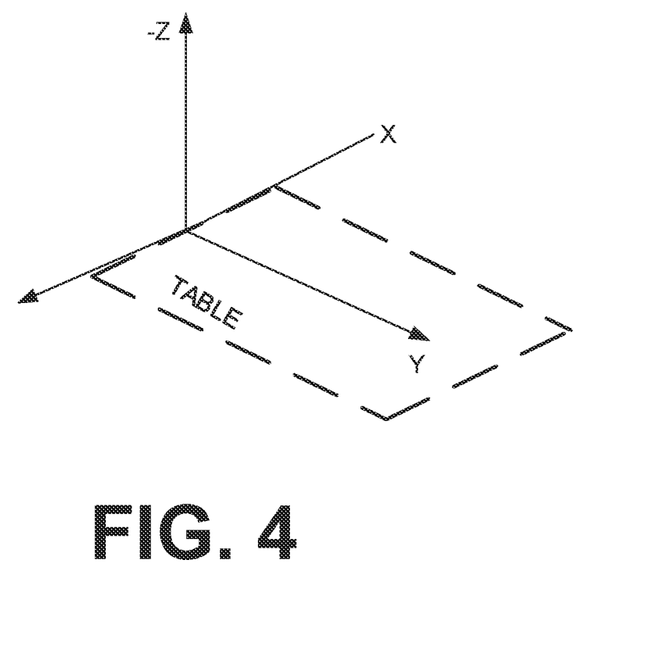
FIG. 4 depicts an example coordinate system in which the DRS device of FIG. 2 can be placed.

In the example of FIG. 4, the coordinate system is shown relative to a table, such as where the patient is placed for a procedure. One of the sensors 26 can be oriented in the y-direction and the other of the sensors 28 can be oriented in the z-direction to enable detection of the worst possible cause of electromagnetic field distortion interference. As an example, the sensors can be orthogonal (90 degrees) to one another. However, the angle between the sensors can be any known angle. In some examples, the three-dimensional coordinate system of FIG. 4 can be a tracking coordinate system (e.g., of tracking system 13). However, the coordinate system may be different from the tracking coordinate system.

For example, the predetermined fixed distance (d1) can be calibrated to zero (or approximately zero) by the tracking system 13 and/or the computing device 14 in the absence of electromagnetic field distortion. For example, the DRS device 12 can be positioned near a region of interest (e.g., on the anterior surface of the patient's body) such that one sensor has an orientation along the HF direction and another sensor has its orientation along the AP direction. The C-arm can be moved to the storage position sufficiently far from the region of interest to remove the effect of its secondary field. In the absence of electromagnetic field distortion, the DRS device 12 will thus report a fixed distance and angle between sensors undisturbed by electromagnetic field distortion. This distance can be stored in memory and subtracted from distance calculation to calibrate the reported distance between sensor coils effectively to zero. The presence of electromagnetic field distortion due to an electromagnetic field interference generated by equipment used within or positioned in close proximity of the volume electromagnetic field provided by the tracking system 13 can result in an electromagnetic field distortion error that can adversely affect sensed position and orientation of sensors being tracked within the controlled electromagnetic field of the tracking system 13. In C-arm angiography, for example, the electromagnetic field distortion can be due to the C-arm position and/or a characteristic of the electromagnetic field generator. Additionally or alternatively, when a metallic object is introduced in the electromagnetic field can affect the field. In response to these or other interfering events, the reported distance between sensor coils (determined by the computing device from tracking data) can be larger (or smaller) than the known distance. The difference between the calibrated distance and the reported distance can correspond to the electromagnetic field distortion error experienced by any of the tracking sensors on a medical device. The same can be true for the fixed angle between sensor coils; namely a difference between the calibrated angle and the sensed angle between sensors can correspond to the electromagnetic field distortion error. In the absence of detecting and, ultimately, correcting the source of the electromagnetic field distortion error, the accuracy of the tracking may be reduced. One or more threshold values thus can be set to establish a level of acceptable accuracy for a given application. For instance, if the difference between the calibrated distance and/or angle and the computed distance or angle exceeds the threshold, in response to influence from a secondary field or other object that causes field distortion, guidance can be provided in the form of warning to the operator.

As illustrated in FIG. 3, the sensor coils 26, 28 are orthogonal (at 90 degrees) relative to each other. However, other angles are possible as long as the angle is known a priori. As an example, one sensor coil 26 can be arranged according to a trajectory of interest in an orientation that is susceptible to electromagnetic field distortion error and the other sensor coil 28 can be arranged in an orientation which is less likely (or not) susceptible to electromagnetic field distortion error. When used in connection with a C-arm angiography procedure, for example, one of the sensor coils 26 can be arranged in congruence with the artery of interest and the other sensor coil 28 can be arranged perpendicular to the artery of interest. When exposed to an interfering electromagnetic field, the at least two sensor coils 26, 28 are configured to separate beyond a predetermined distance of separation. The amount of separation due to the interfering electromagnetic field can be indicative of a level of electromagnetic field distortion error caused by the medical procedure. The electromagnetic field distortion error can be experienced by the tracking sensors, and this electromagnetic field distortion error can influence tracking data and, if not detected and corrected, may result inaccurate positioning of objects within a patient's body.

In examples where the DRS device 12 is placed on a patient's chest and is undergoing respiratory motion, the sensed distance between the sensors 26, 28 that varies over time may be translated in an oscillatory pattern (e.g., by as much as a few cm if located on the anterior surface). The reported inter-sensor distance will also vary due to the distances from the reference sensor to the generator and the source of interference; but this variation will be much lower in magnitude in comparison with the inter-sensor distance associated with the electromagnetic field distortion error. Accordingly, the average position of the sensors 26, 28 over a few breathing cycles can be used to assess the electromagnetic field distortion error while components that may lead to be electromagnetic field distortion error (such as the C-arm and the electromagnetic generator in a C-arm angiography study) is stationary.

The DRS device 12 can output sensor signals for each of the sensor coils 26, 28 to the tracking system 13. The tracking system 13 also receives signals from each tracking sensor on a medical device within a patient's body in response to the electromagnetic field. The sensor coils 26, 28 of the DRS device 12 and tracking sensors (not shown) can provide an output to the tracking system 13 in response to the electromagnetic field, which may include the presence or absence of an interfering field at a constant or varying level. For example, each tracking sensor and DRS sensor 26, 28 can be implemented as a 5 degree of freedom sensor or a 6 degree of freedom sensor. The tracking system 13 includes a field generator 15 to provide an electromagnetic field for a volume of interest in which the tracking sensors and DRS device reside. The tracking system 13 and sensors can be implemented as the types that are commercially available from Northern Digital Inc. of Ontario, Canada. The tracking system 13 is adapted to provide tracking data over time for each sensor based on the respective sensor signals induced in response to the electromagnetic field. The tracking data represents the location and orientation of the tracking sensors within the region of interest of the patient's body in a tracking coordinate system, which can be used likewise to localize the position of the medical device itself.

Figure 5:
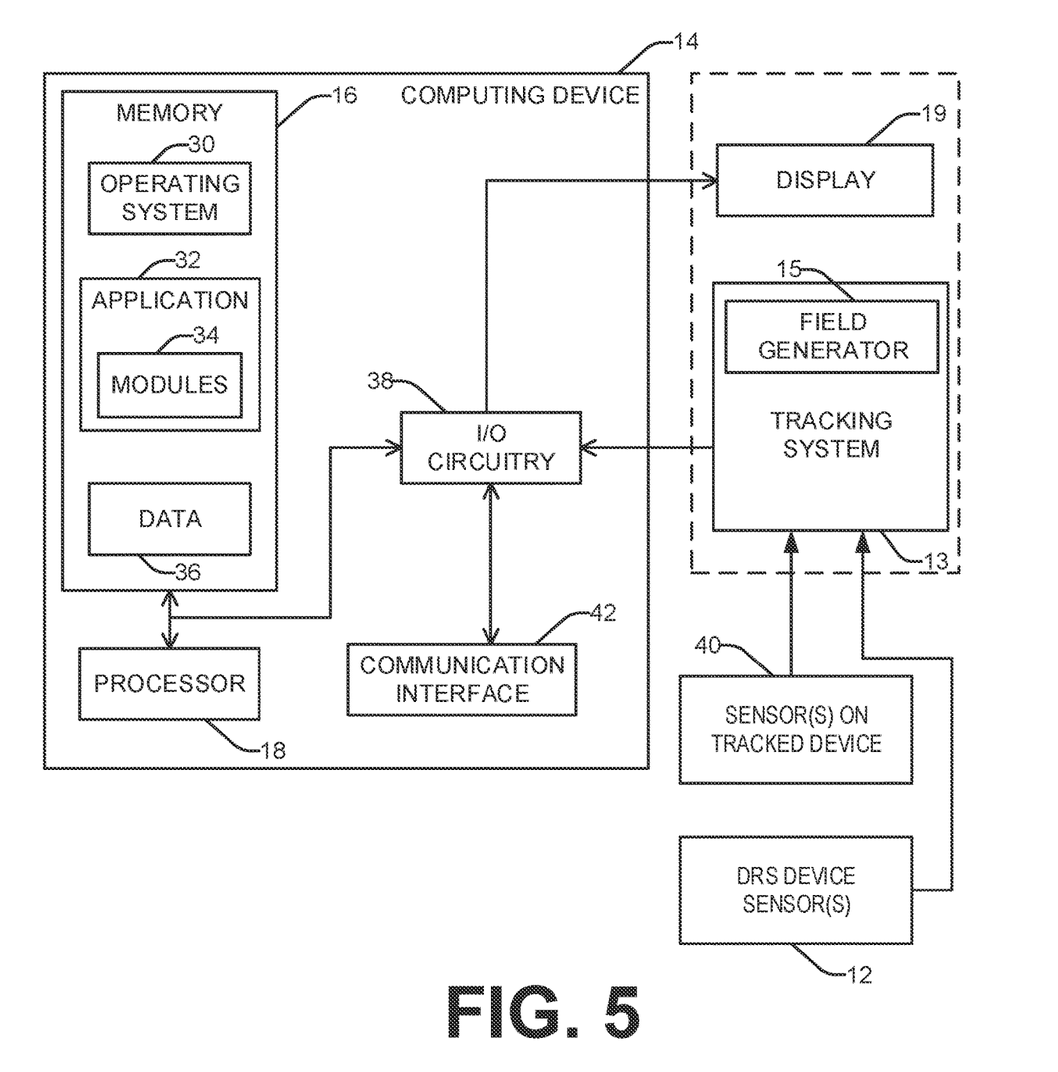
FIG. 5 depicts a block diagram of an example of a computing device that can be used in the system of FIG. 1.

The tracking system 13 can provide data based on the output data from the sensor coils 26, 28 and the tracking data to a computing device 14. The computing device 14 includes a non-transitory memory 16 and a processor 19 to determine a sensed angle and a sensed spatial position of each of the sensor coils 26, 28 in response to application of the electromagnetic field. However, at least part of this determination can also be done at least in part by the tracking system 13. An example of the computing device 14 that can be used in the system 10 is shown in FIG. 5. The computing device 14 can receive inputs through I/O circuitry 38 from the tracking system 13 including (1) data related to the DRS device 12 and/or (2) tracking data related to one or more sensors on tracked medical devices 40. The computing device 14 can also interface with a display device 19 and/or have the display device 19 within the computing device 14. The tracking system 13 and the display device 19 are each communicatively coupled to the computing device 14 (e.g., via I/O circuitry 38).

The computing device 14 can include one or more computing apparatuses that can include a memory 16 and a processor 18. The memory 16 can be a non-transitory computer readable device that can be configured store a variety of machine readable instructions, such as instructions corresponding to an operating system 30 and one or more application programs 32, as well as data 36, including program data, and/or other data. The operating system 30 can be any suitable operating system or combinations of operating systems, which can depend on manufacturer and system to system corresponding to different computer manufacturers. For example, the other data can be input into the computing device 14 or can be acquired for the specific DRS device 12 and/or the machines being used in the medical procedure. While in this example, the relative position and angle between sensors is described as occurring in the computer 14, which may be connected with the tracking system 13 via a tracking interface, in other examples, such computations and other functionality described within the computing device can, wholly or partially, be integrated with the tracking system functionality—either within the tracking system or the computer system.

The memory 16 can be implemented, for example as volatile memory (e.g., RAM), nonvolatile memory (e.g., a hard disk, flash memory, a solid-state drive or the like) or combination of both. It is to be understood that the memory 16 does not require a single fixed memory but the memory can include one or more non-transitory machine-readable memory (e.g., volatile and/or non-volatile memory devices) that can store data and instructions. The memory 16 can store data 36 and/or instructions corresponding to the operating system 30 and/or the applications 32 in a single device or distributed across multiple devices, such as in a network or a cloud computing architecture. The data 36 can also include configuration information related to a threshold, related to the devices used for the medical procedure, including C-arm information and electromagnetic generator information, or any other relevant information.

Figure 6:
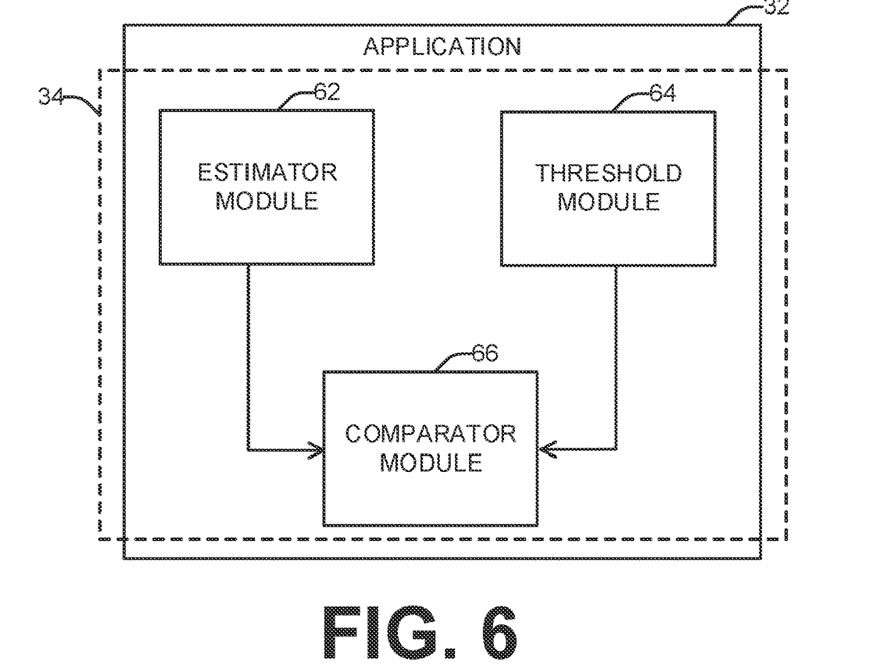
FIG. 6 depicts a block diagram of an application that can be executed by the computing device of FIG. 5.

The processor 18 can be configured to access the memory 16 and execute the machine-readable instructions to perform computations and control functions (e.g., corresponding to the operating system 30 and/or the applications 32). For example, the processor 18 can be configured to access the memory 16 to access an application program 32 and/or the associated program modules (code) 34 include calculator programmed to compute a sensed relative distance and angle between each pair of sensor coils based on the tracking data in response to an electromagnetic field. As mentioned, since the actual relative distance and angle between each pair of sensor coils is known a priori, the program modules 34 can also be programmed to compute a difference between the sensed distance and angle and the predetermined distance and angle. Electromagnetic field distortion can be indicated based on the computed difference between the predetermined angle and the sensed angle and/or the predetermined spatial position and the sensed spatial position. For instance, the occurrence of field distortion is identified if difference between the predetermined angle and the sensed angle and/or the predetermined spatial position and the sensed spatial position exceeds an expected difference value (one or more thresholds). The associated program modules 34 thus can estimate the electromagnetic field distortion error based on the inputs from the DRS device 12. An example of execution of the modules 34 (e.g., by processor 18) is shown in FIG. 6.

An estimator module 62 can be used to provide an estimate of the electromagnetic field distortion based on the inputs (e.g., sensor signals) from the DRS device 12. For example, the estimator module 62 can zero out the predetermined spatial position in three dimensions and/or the predetermined angle of separation, receive a sensed angle and a sensed spatial position, and estimate the electromagnetic field distortion based on a difference between the predetermined values (which are zeroed) and the sensed values.

A threshold can be retrieved from memory (e.g., stored in a table or other data structure in memory) by the threshold module 64. As an example, the threshold can include a spatial distance threshold and/or an angle threshold. The thresholds can be chosen for an operating parameter of the specific tracking system 13, the specific medical devices being used, and/or the specific medical procedure from a chart stored in the memory 16. However, the threshold may be established as a default threshold according to the equipment being used in the medical procedure. A comparator module 66 can compare the calculated distance of separation to a distance threshold to determine whether the electromagnetic field distortion is within tolerable operating parameters. If the calculated distance exceeds the threshold, the current distortion may be considered excessive and outside of normal operating parameters for tracking. Additionally or alternatively, if the calculated angle exceeds the angular threshold, the current distortion may likewise be considered excessive and outside of normal operating parameters for tracking. The comparator module 66 can store information, including the time and whether the electromagnetic field distortion satisfies or exceeds the threshold, in the memory 16 as data 34 representing the presence of field distortion.

Based on the comparison, comparator module 66 and/or another application 32 can determine whether the electromagnetic field distortion error is acceptable or unacceptable. When the electromagnetic field distortion error is unacceptable (e.g., the estimated electromagnetic field distortion error is greater than the desired distortion electromagnetic field distortion error), in some examples, the computing device 14 can issue a warning. The warning can include one or more of a tactile indication, an audio indication, a visual indication, or the like. The warning can also be logged and stored in the memory 16 as a record of the unacceptable electromagnetic field distortion error. For example, the warning can be a message or graphic on the display 19. When the estimated distortion error is determined to be unacceptable, the computing device 14 can suggest a position of various components contributing to the electromagnetic field distortion error that would decrease the electromagnetic field distortion error to an acceptable level. In the case of a C-arm angiography procedure, for example, the computing device 14 can suggest a C-arm angulation and/or a generator position. A surgeon can make the suggested adjustments to reduce the electromagnetic field distortion error. However, in some examples, the adjustments can be made automatically by actuation of a motion system that is coupled to the C-arm, such as a mathematical adjustment made with or without alerting a user. In other examples, in response to the warning issued by the computing device, a user can move the C-arm to an arbitrary position until the warning terminates.

As a further example, for a C-arm angiography procedure, the DRS device 12 can be determined to be in the correct orientation when an angle between the DRM device longitudinal axis and an EM alignment axis is within an acceptable alignment threshold. For example, angles may be determined as an inverse cosine function as follows and compared (by comparator module 66) to angular alignment thresholds (by threshold module 64) as follows:

$$\cos^{-1}\{Rz,_{long\ axis\_z}\cdot(0,0,-1)\} < T_{\theta Ry},\ \text{and}$$

$$\cos^{-1}\{Ry,_{long\ axis\_z}\cdot(0,1,0)\} < T_{\theta Rz},$$

where the dot products are normalized, $T_{\theta Ry}$ and $T_{\theta Rz}$ are acceptance angular thresholds defined in the in a configuration table (e.g., stored in memory 16), and $Rz,_{long\ axis\_z}$ and $Rz,_{long\ axis\_z}$ are estimated positions derived (by estimator module 62) from the 5DOF reported quaternions in tracking data (e.g., from tracking system 13).

If the comparator module determines that one or both of the computed angles exceeds the alignment threshold $T_{\theta Ry}$ or $T_{\theta Rz}$ then an indication may be provided to alert the user to adjust the alignment between the DRS device and the EM alignment axis. This adjustment alert may be visual and/or audible.

As a further example, criteria for a generating a warning message (e.g., visual, audible and/or tactile) can be determined (e.g., by program modules 34) as follows:
if $$\{\text{dist}\{Rz,Ry\} > T_{dist}\ \text{and Angle}\{Sr,(0,0,-1)\} < T_{\theta z}\ \text{and}\ Z\text{pos}[Sr] < T_z\}$$

where,

Sr corresponds to any EM sensor from a sensor-equipped device, and dist{Rz,Ry} is a Euclidean distance between sensors (e.g., sensor coils) that can be expressed as follows:

$$\text{dist}\{Rz,\ Ry\} = \sqrt{\begin{bmatrix} [(Rz.x - Rz.x,\ c\ln) - (Ry.x - Ry.x,\ c\ln)]^2 + [(Rz.y - Rz.y,\ c\ln) - \\ (Ry.y - Ry.y,\ c\ln)]^2 + [(Rz.z - Rz.z,\ c\ln) - (Ry.z - Ry.z,\ c\ln)]^2 \end{bmatrix}}$$

and "Angle" is based on the vector along the long axis of sensor in EM coordinates (converted from the reported quaternion), $T_{dist}$, $T_{\theta z}$, $T_z$ are respective distance and angular defined in the threshold module 64, $R_z$ and $R_y$ are 3D positions of orthogonal DRS sensors (e.g., along z and y orientations, such as shown in FIGS. 3 and 4), (0,0,−1) in EM coordinates (pointing Posterior to Anterior, with patient supine).

In other examples, difference distance and angular computations may be used to determine the relative position and angle of the DRS sensors.

Figure 7:
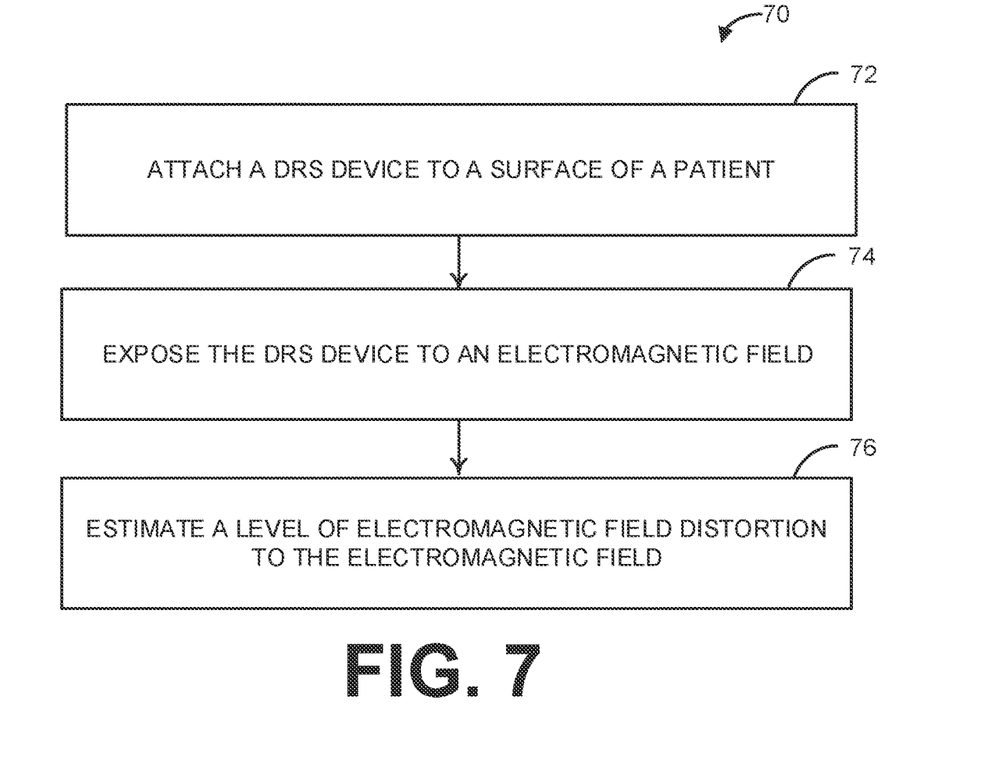
FIG. 7 depicts a process flow diagram of an example method for detecting an electromagnetic field distortion.
Figure 8:
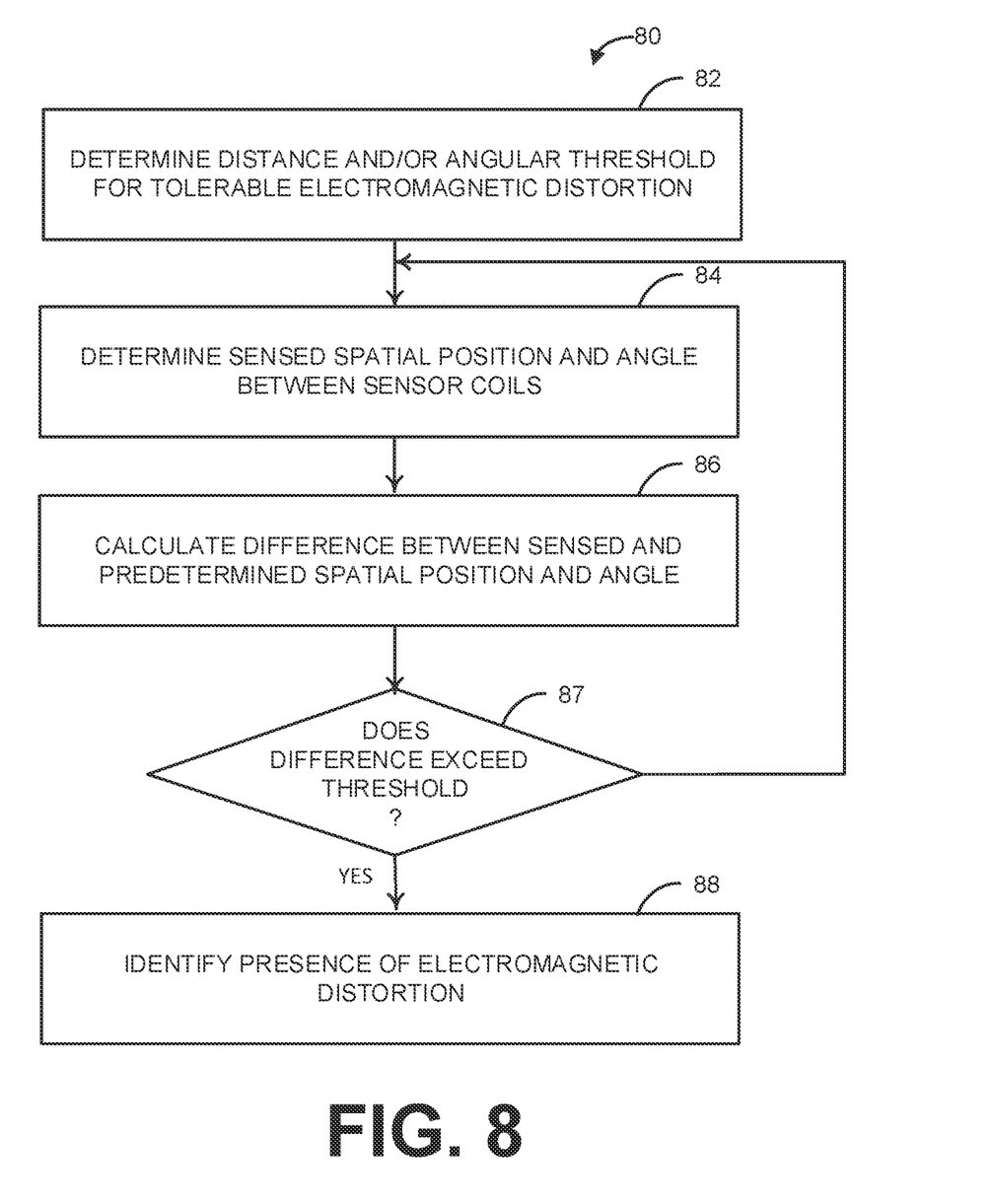
FIG. 8 depicts a process flow diagram of an example method for mitigating electromagnetic field distortion.
Figure 9:
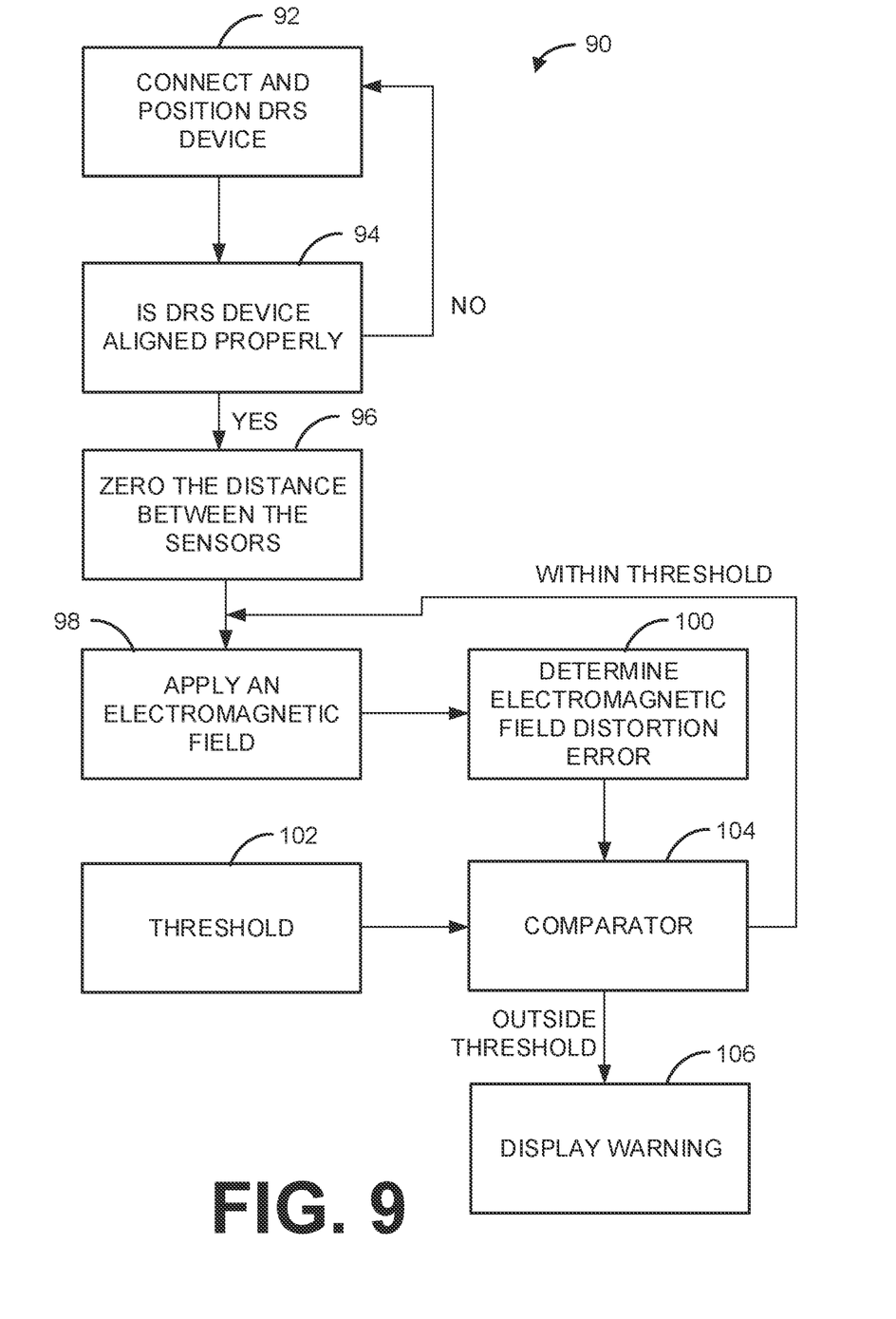
FIG. 9 depicts a process flow diagram of an example method for detecting an electromagnetic field distortion and alerting a user of the electromagnetic field distortion.

In view of the foregoing structural and functional features described above, methods 70, 80, and 90 in accordance with various examples of the present invention will be better appreciated with reference to FIGS. 7, 8, and 9, respectively. While, for purposes of simplicity of explanation, the methods 70, 80, and 90 are shown and described as executing serially, it is to be understood and appreciated that the methods 70, 80, and 90 are not limited by the illustrated order, as some actions could occur in different orders and/or concurrently with other examples from that shown and described herein. Moreover, not all illustrated features may be required to implement the methods 70, 80, and 90. It will be appreciated that some or all of each of these methods 70, 80, and/or 90 can be implemented as machine-readable instructions on a non-transitory computer readable medium (e.g., as one or more applications 30 stored in the non-transitory memory 16 and executable by the processor 18).

FIG. 7 depicts a method 70 for detecting an electromagnetic field distortion. The electromagnetic field distortion can be detected using a DRS device (e.g., DRS device 12) For example, as described above, the DRS device includes at least two sensor coils arranged at a predefined angle relative to each other and at a predefined spatial position in three-dimensional space. In some instances, the DRS device can include three or more sensor coils to increase detection accuracy. The DRS device can be arranged and oriented relative to the patient and/or arranged relative to the imaging device (e.g., a C-arm) and a tracking system.

At 72, the DRS device is attached to a surface of a patient. The DRS device can be attached to the patient's skin surface. As an example, the DRS device can be attached to the skin surface adjacent a region of interest within the patient (e.g., a portion of the patient to be imaged). As another example, the DRS device can be attached to the operating table proximal to the patient. At 74, the DRS device can be exposed to an electromagnetic field. The DRS device can provide an input (one or more sensor signals) to a tracking system and/or a computing device. A sensed angle and a sensed spatial position in a three-dimensional space can be determined based on the input from the DRS device. At 76, a level of electromagnetic field distortion due to the electromagnetic field can be estimated. The level of electromagnetic field distortion can be estimated based on a difference between the sensed angle and the predetermined angle and/or the sensed spatial position and a predetermined spatial position.

The distortion error can be graphically displayed to the user, for example with error bars or another graphical indicator that varies over time based on the detected distortion estimated at 76. For example, the computing device can determine whether the electromagnetic field distortion error corresponds to a tolerable distortion error or whether the electromagnetic field distortion error will cause an unacceptable error in tracking the medical device.

FIG. 8 depicts a method 80 for mitigating electromagnetic field distortion. The method 80 may be a computer-implemented method. For example, the method 80 can be stored on a non-transitory computer readable medium and executed by a processor to cause a computing device (e.g., computing device 14) to perform operations of the method 80 (as shown in acts 82-88). The method 80 can be used to determine whether an electromagnetic field distortion error is tolerable or not.

At 82, a distance and/or angular threshold for a tolerable electromagnetic field distortion can be determined and/or retrieved from memory. The limits for the tolerable distortion error can be determined and/or retrieved by the computing device based operation parameters of the tracking device, on the physiology and/or a task under consideration and/or one or more of the devices being used. However, in some examples, the limits can be programmed by a user (via user input device). At 84, a sensed spatial position and angle between sensor coils can be determined. The determination can be made based on data provided to a tracking system or a computing device in response to DRS sensor signals. At 86, differences between sensed and predetermined spatial positions and angles of DRS sensors can be calculated. At 87, it can be determined whether the calculated difference exceeds one or more thresholds. If the difference does not exceed the one or more thresholds, the method 80 can revert to 84. If the difference does exceed the one or more thresholds, the method 80 can proceed to 88, where the presence of electromagnetic distortion is identified. The electromagnetic distortion can be displayed as a visualization on an output device, an audible message or a tactile indication (e.g., by gently vibrating a handle or gripper of an endovascular device).

As an example, an adjustment can be suggested if the electromagnetic field distortion error is not a tolerable electromagnetic field distortion error. The suggestion can also be output on the visualization on the output device. If the electromagnetic field distortion error is deemed intolerable, the suggested adjustment can be adjusting a system used for the medical procedure and/or the tracking system. For example, an angulation related to a moveable component of an imaging system (e.g., a C-arm) and can be suggested, and a surgeon or other user can make the suggested adjustment. In other examples, the suggested adjustment can be made automatically. As an example, instead of or in addition to suggesting an adjustment, when the electromagnetic field distortion error is not a tolerable distortion error, a warning message (e.g., a tactile indication, an audio indication, a visual indication, or the like) can be issued with the visualization. However, if the electromagnetic field distortion error is determined to be tolerable, no further actions are taken to correct the electromagnetic field distortion error, and any warning or other indication may be terminated.

FIG. 9 depicts a method 90 for detecting an electromagnetic field distortion and alerting a user of the electromagnetic field distortion to track a medical device during a medical procedure with a higher accuracy. At 92, a user can connect and position the DRS device. The user can connect the DRS device to a computing device and position the DRS device (e.g., on a patient's skin surface proximal to a region of interest for the medical procedure). At least two sensors within the DRS device are placed relative to each other. Since the DRS device is placed relative to a patient, the DRS device is placed relative to one or more systems to complete the medical procedure. For example, when the medical procedure is a C-arm angiography procedure, the DRS device is placed relative to the orientation of the C-arm device. In the example of a C-arm angiography procedure, at least one of the sensors of the DRS device can be arranged in a direction of a vessel being studied in the region of interest. Another of the sensors in the DRS device can be arranged at an angle relative to the sensor arranged in a direction of the vessel being studied. In an example, the at least two sensors can be arranged orthogonally to each other with an angle of 90 degrees. In other words, the other sensor in the DRS device can be arranged orthogonal to the direction of the vessel being studied.

At 94, the alignment of the DRS device can be verified. For example, it can be determined whether the DRS device is centered relative to the region of interest and/or the sensors within the DRS device are aligned with the target for the medical procedure. If the alignment is not proper, the method 90 can return to 92 and reposition the DRS device. If the alignment is proper, the method 90 can proceed to 96.

At 96, the distance between the sensors in the DRS device can be zeroed or normalized. The sensors can have predefined angle and a predefined spatial position in a three-dimensional coordinate system can be accounted for. At 98, an electromagnetic field can be applied to the DRS device and the surrounding body. At 100, an electromagnetic field distortion error can be determined. For example, the electromagnetic field distortion error can be determined based on a difference between a sensed angle and a predetermined angle between sensors of the DRS device and/or a difference between a sensed relative spatial position and a predetermined relative spatial position for each pair of sensors in the DRS device. At 104, a comparator can compare the electromagnetic field distortion error to one or more thresholds 102 to determine whether the electromagnetic field distortion error exceeds the threshold level. If the electromagnetic field distortion error is within (or less than) the threshold, the method 90 can continue to apply the electromagnetic field 98. However, if the electromagnetic field distortion error is outside the threshold (or exceeds the threshold), a warning or other indication can be provided at 106. The warning can be a message displayed together with a visualization that includes one or more suggestions for reducing a level of the electromagnetic field distortion error. The warning can include one or more of a tactile indication, an audio indication, a visual indication, or the like. The warning can also be logged and stored in a non-transitory memory as a record of the electromagnetic field distortion error. Thus, as disclosed herein, by detecting and adjusting equipment, electromagnetic distortion can be mitigated and thereby help to facilitate accurate tracking of other devices by an electromagnetic tracking system.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
   a distortion reference sensor (DRS) device attachable to a surface adjacent a region of interest at a known orientation relative to a patient and external to the patient, the DRS device comprising at least two sensors that include first and second sensors that are arranged at a predetermined angle, at a predetermined distance, and at a predetermined spatial position in three-dimensional space relative to each other, wherein the predetermined distance between the first and second sensors is changed to a new distance in response to being exposed to an interfering electromagnetic field; and
   a computing device to determine the new distance between the first and second sensors based on tracking data representing the position and orientation of each of the first and second sensors in a three-dimensional coordinate system, the tracking data being generated by a tracking system,
   wherein the computing device is to compare the new distance between the first and second sensors to a baseline distance for the first and second sensors to compute a difference distance value that is indicative of an electromagnetic field distortion error, the baseline distance corresponding to the predetermined distance.

2. The system according to claim 1, further comprising the tracking system coupled to each of the at least two sensors to receive sensor signals in response to application of the interfering electromagnetic field.

3. The system of claim 1, wherein the predetermined angle is approximately 90 degrees.

4. The system of claim 1, wherein the DRS device further comprises an attachment medium configured to affix the DRS device to the surface adjacent to the region of interest.

5. The system of claim 1, wherein the DRS device is attachable to the surface adjacent to the region of interest and having an axis aligned with at least one structure within the region of interest.

6. The system of claim 5, wherein by aligning the DRS device with the at least one structure within the region of interest, the DRS device is oriented relative to a moveable arm of an imaging system.

7. The system of claim 1, further comprising a display device in communication with the computing device to provide a warning message when the difference distance value that indicative of the electromagnetic field distortion errors exceeds a threshold difference value.

8. The system of claim 7, wherein the warning message comprises at least one of a tactile indication, an audio indication, and a visual indication.

9. The system of claim 1, wherein the DRS device comprises at least three sensors arranged at the predetermined angle and at the predetermined spatial position in three-dimensional space relative to each other.

10. The system of claim 1, wherein the first sensor is aligned in a first direction along an anterior-posterior (AP) direction of the patient, and the second sensor is aligned in a second direction along a head-foot (HF) direction of the patient.

11. The system of claim 10, wherein the DRS device is oriented relative to a moveable arm of an imaging system, such that the moveable arm and the first sensor are aligned to extend in the AP direction of the patient, wherein the moveable arm generates the interfering electromagnetic field, and the tracking data includes sensor measurements generated by the first and second sensors when the first sensor and the moveable arm extend in the AP direction of the patient, wherein the computing device determines the position of moveable arm relative to the DRS device based on the sensors measurements when the first sensor and the moveable arm extend in the AP direction of the patient.

12. The system of claim 11, wherein an alignment of the moveable arm in a same direction as the first sensor increases a sensitivity of the first sensor to eddy currents from the moveable arm, wherein the increase in the sensitivity of the first sensor to the eddy currents is captured in the sensor measurements.

13. The system of claim 12, wherein the moveable arm is a C-arm.

14. The system of claim 1, wherein the DRS device is attachable to the surface of the patient corresponding to a chest of the patient that is undergoing respiratory motion over a plurality of respiratory cycles,
wherein the tracking data comprises spatial position information for each of the first and second sensors over the plurality of respiratory cycles,
wherein the computing device is to average the spatial position information for each of the first and second sensors to generate average spatial position information for each of the first and second sensors over the plurality of respiratory cycles, and
wherein the computing device is to determine the new distance between the first and second sensors based on the average spatial position information for each of the first and second sensors.

15. The system of claim 1, wherein the computing device is to evaluate an angle between a longitudinal axis of the DRS device and an electromagnetic (EM) alignment axis of a moveable arm of an imaging system relative to an alignment threshold.

16. The system of claim 15, wherein the computing device is to provide an indication that the angle between the longitudinal axis of the DRS device and the EM alignment axis of the moveable arm exceeds the alignment threshold, wherein the moveable arm generates the interfering electromagnetic field, the indication being one of a visual and audible alert.

17. The system of claim 15, wherein the computing device is to cause a position of the moveable arm to be adjusted to a new position relative to the DRS device to reduce an impact of the interfering electromagnetic field generated by the moveable arm on the DRS device corresponding to a reduction in the electromagnetic field distortion error.

18. The system of claim 17, wherein the computing device causes actuation of a motion system that is coupled to the moveable arm to cause the position of the moveable arm to be changed to the new position relative to the DRS device.

19. A method comprising:
attaching a distortion reference sensor (DRS) device to a surface, adjacent a region of interest at a known orientation relative to a patient and external to the patient, the DRS device comprising at least two sensors that include first and second sensors that are arranged at a predetermined angle, at a predetermined distance, and a predetermined spatial position in three-dimensional space relative to each other;
exposing the DRS device to an interfering electromagnetic field;
determining a new distance between the first and second sensors based on tracking data representing the position and orientation of each of the first and second sensors in a three-dimensional coordinate system in response to being exposed to the interfering electromagnetic field, wherein the interfering electromagnetic field changes the predetermined distance between the first and second sensors to the new distance;
comparing the new distance between the first and second sensors to a baseline distance for the first and second sensors to compute a difference distance value that is indicative of an electromagnetic field distortion error, the baseline distance corresponding to the predetermined distance.

20. The method of claim 19, wherein one of the at least two sensors is arranged in a direction of a vessel being studied in the region of interest.

21. The method of claim 20, wherein another of the at least two sensors is arranged orthogonally to the direction of the vessel being studied, and
wherein the predetermined angle is approximately 90 degrees.

22. The method of claim 19, wherein the difference distance value is a distance vector in the three-dimensional coordinate system.

23. The method of claim 19, further comprising displaying, by the system, a visualization related to the electromagnetic field distortion on an output device.

24. The method of claim 23, further comprising providing at least one suggestion to reduce the estimated electromagnetic field distortion, wherein the at least one suggestion comprises at least one of an angulation of a moveable arm of an imaging system and a position of an electromagnetic generator.

25. The method of claim 23, wherein the visualization comprises at least one of an audio indication, and a visual indication.

26. The method of claim 19, wherein DRS device comprises at least three sensor coils arranged at the predetermined angle and at the predetermined spatial position in three-dimensional space relative to each other.

* * * * *